US006985220B1

(12) United States Patent
Chen et al.

(10) Patent No.: US 6,985,220 B1
(45) Date of Patent: Jan. 10, 2006

(54) INTERACTIVE THRESHOLD TUNING (75) Inventors: Chien-Huei Chen, San Jose, CA (US); Vivek Bhagat, Santa Clara, CA (US); Qiang Song, San Jose, CA (US); James A. Quigley, Mountain View, CA (US); Ashok V. Kulkarni, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 296 days.

(21) Appl. No.: 10/644,319

(22) Filed: Aug. 20, 2003

(51) Int. Cl.
*G01N 21/88* (2006.01)
(52) U.S. Cl. .................................... 356/237.5
(58) Field of Classification Search .. 356/237.1–237.6; 250/214 AG
See application file for complete search history.

(56) References Cited

U.S. PATENT DOCUMENTS 6,563,114 B1 * 5/2003 Nagahama et al. ......... 250/310
6,833,913 B1 * 12/2004 Wolf et al. ............... 356/237.2

* cited by examiner

*Primary Examiner*—Tu T. Nguyen
(74) *Attorney, Agent, or Firm*—Luedeka, Neely & Graham, P.C.

(57) ABSTRACT

A method of tuning an inspection system. An inspection piece is sensed and analyzed to identify anomalies. Level information is analyzed with an initial set of thresholds, and an initial portion of the anomalies are flagging as defects. The inspection system parameters are changed, and the level information is analyzed with a modified set of thresholds. The anomalies are flagged as defects based on the immediately preceding analysis of the level information. The steps of changing the thresholds and reflagging the defects are repeated as desired, and the modified set of thresholds are stored for use in an inspection system recipe.

19 Claims, 4 Drawing Sheets

F*i*() versus P1

Fig. 3

F*i*() versus P2

Fig. 4

F*i*() versus P*n(i)*

INTERACTIVE THRESHOLD TUNING

The U.S. Government has a paid-up license in this invention and the right in limited circumstances to require the patent owner to license others on reasonable terms as provided for by the terms of contract 70NANB0H3038, awarded by NIST.

FIELD

This invention relates to the field of integrated circuit fabrication. More particularly, this invention relates to optimizing the operational parameters of inspection equipment used during integrated circuit fabrication.

BACKGROUND

Integrated circuit fabrication relies heavily on frequent and consistent inspection of the structures formed at various stages during the fabrication process. Some of the inspections can be electronic or chemical in nature, but a great many of the inspections that are performed are optical in nature. In other words, the substrates or semiconductor wafers on which the integrated circuits are formed are inspected by collecting electromagnetic radiation such as light received from the substrate, whether that light be reflected from or transmitted through the substrate, and inspecting the properties of the collected light.

Most optical inspections in this day are accomplished by digitizing the collected light and then analyzing the digitized images with sophisticated computerized analytical routines, which compare the images to one or more of a variety of baseline or standardized references, and then detect differences between the captured images and the references. The routine then further attempts to identify the nature of any differences so detected. This general process is typically very helpful to process engineers and others who are responsible for monitoring and improving both the integrated circuits so formed and the processes by which they are fabricated.

However, there are several inherent difficulties in such an optical inspection process. One general class of issues deals with the issue of how closely to inspect the substrate. For example, optics having greater magnification will detect smaller and smaller flaws. Light of smaller wavelength will also detect smaller flaws in the substrate. A sensor having a higher resolution, such as a charge couple device having a greater number of and smaller-sized pixels, can also detect smaller flaws. Further, software routines can be set using a variety of different parameters to, at one end of the spectrum, flag every difference between a substrate image and a reference as a defect, and at the other end of the spectrum, ignore all but the very largest of differences. Thus, some degree of tuning or optimization of the inspection equipment is typically performed.

Typically, users optimize inspection recipes in a very laborious trial and error procedure. Starting with any desired recipe, such as a set of threshold parameters that control the sensitivity of an inspection scan, the user runs the inspection with the recipe and then reviews the defects caught by the inspection. If the inspection doesn't catch enough defects of interest, the user lowers or otherwise adjusts one or more threshold parameter. On the other hand, if the recipe caught too many anomalies which were not of interest, the user increases or otherwise adjusts one or more threshold. The user then rescans the substrate with the modified recipe and reviews the inspection result again. The user repeats these three steps of tweaking parameters, rescanning the substrate, and reviewing the result, until he arrives at an acceptable set of threshold values.

The inefficiency of this old method becomes much worse for more advanced defect detection algorithms, such as the segmented auto threshold algorithm of the bright field machines made by KLA-Tencor Technologies Corporation of Santa Clara, Calif., that require many threshold parameters, and the number of iterations is multiplied by the number of threshold parameters.

The first problem with the old methods is the long setup time. Both scanning the substrate and reviewing the results can take a long time and lots of effort. The second problem is that the resulting recipes are usually far from optimal. One reason for this is that when using this manual optimization method, the machine provides very little if any information about the defects, and the user doesn't know how or how much more the recipe can be improved. As a result, the user essentially has to count on his intuition or experience in adjusting the parameters, and usually settles on a set of values that are far from optimal. In addition, because the manual method is so time consuming, many users get to a certain level of optimization, and then just quit.

What is needed, therefore, is a system by which parameter threshold optimization can be more easily accomplished and thereby produce better results.

SUMMARY

The above and other needs are met by a method of tuning an inspection system. Characteristics of an inspection piece are sensed using the inspection system, and the sensed characteristics are analyzed to identify anomalies having location information and level information. The level information of the anomalies is analyzed with an initial set of thresholds of inspection system parameters, and an initial portion of the anomalies are flagged as defects based on the analysis of the level information. A summary of the flagged anomalies is displayed, and an operating curve of potential flagged defects versus threshold for at least one of the inspection system parameters is also displayed. Then at least one of the inspection system parameters is selectively changed to form a modified set of thresholds of the inspection system parameters, and the level information of the anomalies is analyzed with the modified set of thresholds of the inspection system parameters. An updated portion of the anomalies is flagged as defects based on the immediately preceding analysis of the level information, and a summary of the flagged anomalies is displayed. The steps of selectively changing the thresholds and reflagging the defects are repeated as desired, and the modified set of thresholds of the inspection system parameters are stored for use in an inspection system recipe.

In this manner, the system enables users of inspection systems, such as bright field inspection systems, to efficiently and effectively optimize inspection recipes. The system collects special runtime data, such as the level information, produced during a substrate scan, and then provides an informative and interactive graphical user interface environment that enables the user to tune the threshold parameters of the recipe and get real time feedback on the effect of the tuned thresholds, without rescanning the substrate. Thus, the present system provides immediate feedback on the effects of changing the system parameter thresholds, and enables the user to quickly tune the inspection system to increase and preferably maximize the flagging of the defects of interest, while reducing and preferably eliminating the flagging of anomalies in which there is no interest.

In various preferred embodiments, the inspection system is an optical inspection system. The inspection piece is preferably a semiconducting wafer. Preferably, the characteristics of the inspection piece are surface defects. In a preferred embodiment, a spatial representation of the flagged anomalies on the inspection piece is selectively displayed.

According to another aspect of the invention there is described an inspection system having sensors adapted to sense characteristics of an inspection piece. A processor analyzes the sensed characteristics to identify anomalies having location information and level information, analyzes the level information of the anomalies with an initial set of thresholds of inspection system parameters, and flags as defects an initial portion of the anomalies based on the immediately preceding analysis of the level information. A display displays a summary of the flagged anomalies and an operating curve of potential flagged defects versus threshold for at least one of the inspection system parameters. An input selectively changes the at least one of the inspection system parameters to form a modified set of thresholds of the inspection system parameters. The processor further analyzes the level information of the anomalies with the modified set of thresholds of the inspection system parameters, and flags as defects an updated portion of the anomalies based on the immediately preceding analysis of the level information. The display further displays an updated summary of the flagged anomalies. A memory stores the modified set of thresholds of the inspection system parameters for use in an inspection system recipe.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
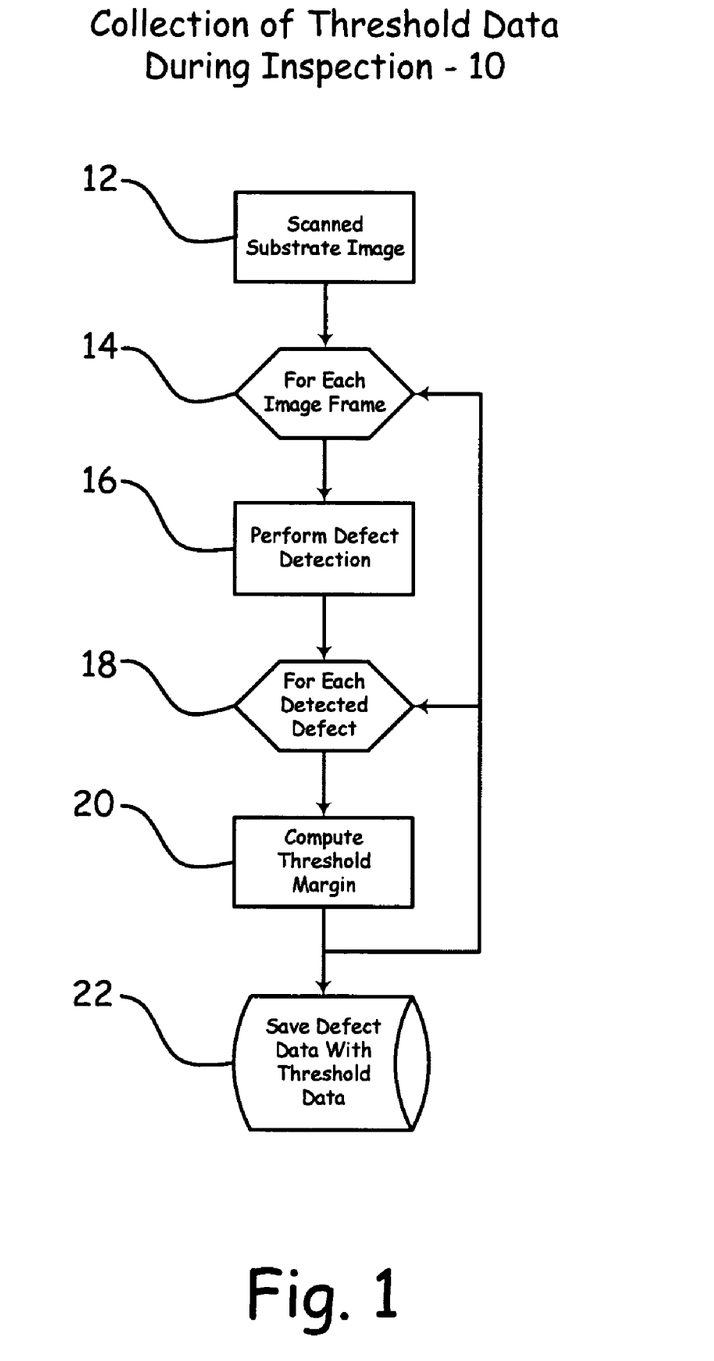
FIG. 1 is a flowchart of a method for collection of threshold data during inspection of a substrate, according to a preferred embodiment of the invention.

With reference now to FIG. 1, there is depicted a method 10 of collecting threshold data during an inspection scan, such as the optical inspection of a substrate. However, it is appreciated that the methods and devices as described herein can also be applied to inspection types other than optical, and inspection objects other than substrates.

The method 10 preferably commences with a scan of the substrate as given in block 12. The substrate scanning step is the step in which information in regard to the inspection piece, in this case an integrated circuit substrate, is gathered, which in this case means capturing the optical images, such as with a charge coupled device filtered to accept a given range of wavelengths of light, such as visible light. Step 14 of the method 10 is an entry point for a portion of the method that is repeated for each image frame of the substrate that is captured, including step 16, where the detection algorithms are employed to flag any detected anomalies as defects.

Step 18 of the method 10 is an entry point for a smaller portion of the method 10 that is repeated for each defect that is detected in the frame currently being analyzed, including step 20, where at least one threshold margin is computed for the defect. This information, both the designation of a flagged defect as determined in step 16, and the computed threshold margin or level information as determined in step 20, is saved as frame data in step 22 of the method 10. The routine then cycles through to determine the threshold data for each defect detected, and then cycles through each frame to determine all the defects in all of the frames. Thus, the method 10 collects and stores not only data in regard to identified defects, but also data in regard to a relative level of a detected anomaly, and the level of the anomaly in regard to the threshold of the parameter by which it was, or was not, flagged as a defect.

Figure 2:
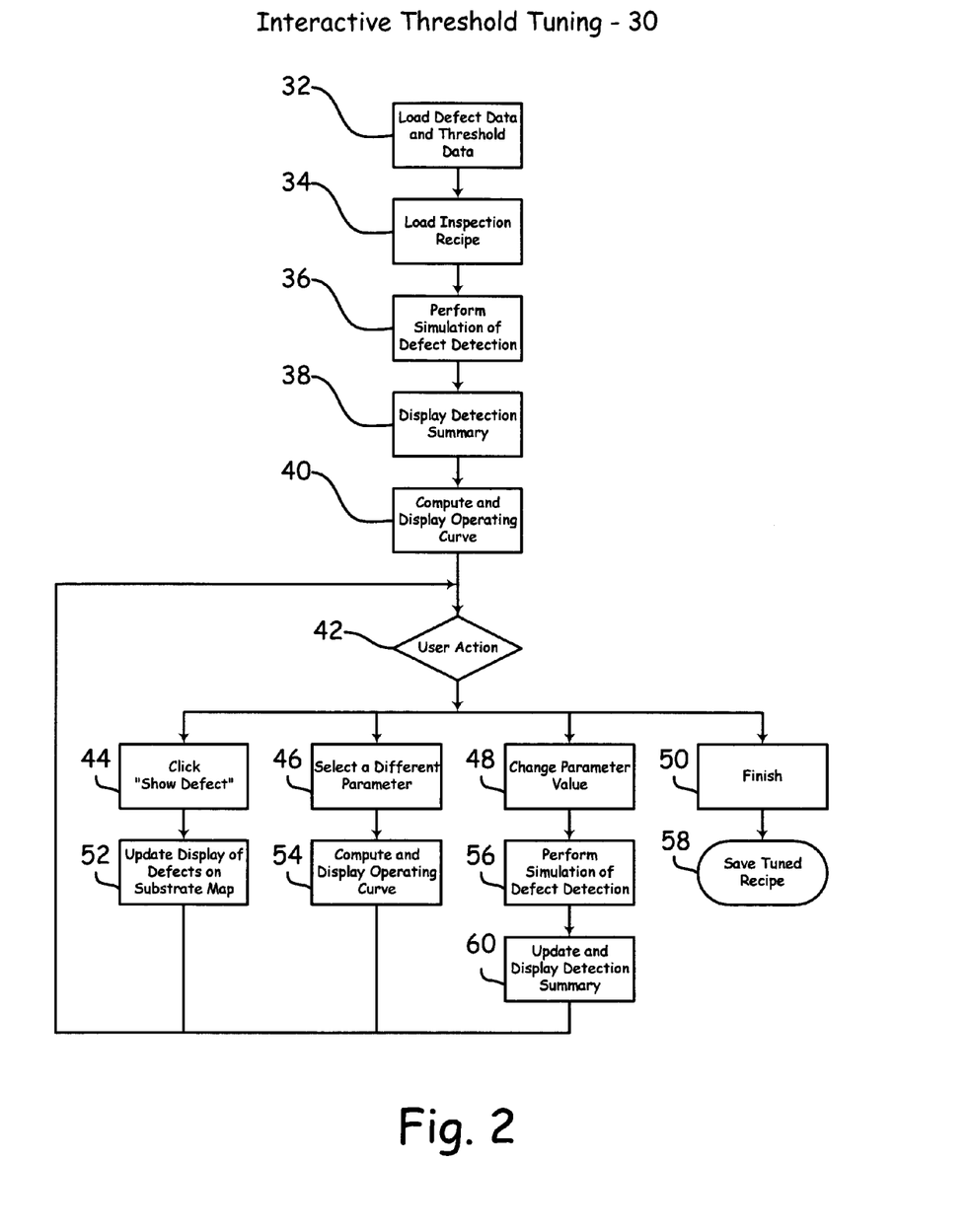
FIG. 2 is a flow chart of a method for interactive threshold tuning, according to a preferred embodiment of the invention.

With reference now to FIG. 2, there are depicted the steps of the method 30 for interactive threshold tuning, or optimization, of the defect detection routine that is employed such as in step 16 of the method 10. The purpose of the method 30 is to optimize the settings of the various parameters used in the defect detection routine 16, so that most preferably real defects which affect yield are detected and flagged as defects, and other anomalies which do not affect yield are either not detected or are not flagged as defects.

The method 30 commences by loading the frame data, including the defect data and the threshold data collected and stored as a part of the method 10, as given in block 32. In step 34, the inspection recipe, or in other words the set of parameters controlling the defect detection function used such as in step 16 of the method 10, is also loaded. A simulation of the defect detection process is accomplished as given in block 36, whereby the threshold values specified in the inspection recipe are applied to the frame data, and the results, such as a summary, of the simulated detection are displayed as given in block 38.

Figure 3:
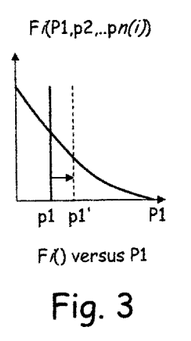
FIG. 3 is a chart of a defect detection function with respect to a first parameter and the effect of changing the first parameter.
Figure 4:
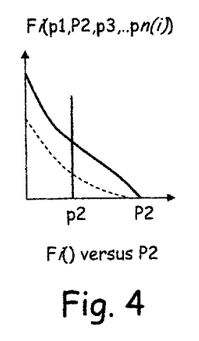
FIG. 4 is a chart of the defect detection function with respect to a second parameter and the effect of changing the first parameter.
Figure 5:
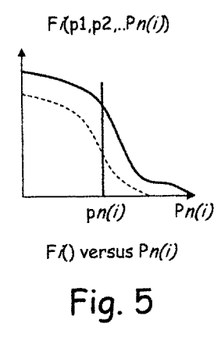
FIG. 5 is a chart of the defect detection function with respect to an nth parameter and the effect of changing the first parameter.
Figure 6:
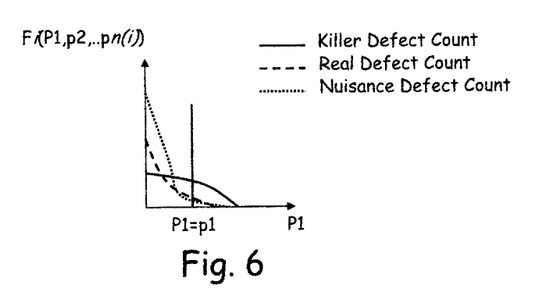
FIG. 6 is a chart of the defect detection function with respect to the first parameter, and the effect of changing the first parameter on defect type.

In addition to displaying the results of the detection operation, operating curves for the various input parameters of the detection routine or recipe are also computed and displayed, as given in block 40. The operating curves depict information such as that generally represented in FIGS. 3–6. FIG. 3 depicts a chart of a function, such as the count of defects detected in step 16 of the method 10, versus the value of an input parameter or threshold P1. The chart depicts a curve showing the relationship between the defects detected by the function at various values of P1, such as p1 and p1'. FIG. 4 depicts similar information for an input P2, and FIG. 5 depicts similar information for an input Pn(i). FIG. 6 depicts the output of the defect detection function for various values of P1, broken down into defect types, such as killer defects, real defects but not killers, and nuisance defects which are detected anomalies but not defects at all.

Once the information as described above has been depicted, such as in the graphical interface of a computing device connected to inspection equipment, either locally or remotely, the system prompts the user to take one of the allowable actions, as given in block 42 of the method 30 depicted in FIG. 2. As depicted in FIG. 2, the allowable actions include the ability to show the defects as given in block 44, select a different parameter for investigation or optimization as given in block 46, change a parameter value as given in block 48, or complete the optimization process as given in block 50. After any one of these various options is selected and accomplished, except of course for finishing the routine as given in block 50, the routine returns to block 42 to await further user instruction. Each of these options is described in more detail below.

When the user selects the option to show the defects, as given in block 44, the system updates a display of defects on a substrate map as given in block 52, such as a spatial display with the representation of the substrate, and markings indicating defects. Additional information may also be presented, such as indicating defect type such as by color or differing defect indication indicia on the substrate map. This provides a visual feedback to the user for the current results of the optimization procedure 30.

Different parameters for optimization are selected in block 46 which, when selected, computes and displays an operating curve as given in block 54, such as depicted in FIGS. 3–6. Different values for the various parameters can be changed as given in block 48. When a parameter threshold is changed, the system performs another simulation of the defect detection routine as given in block 56, updates the display of the summary of the defect detection routine as given in block 60, and awaits further input from the user. When the optimization routine is exited as given in block 50, the current threshold values for the various parameters are saved as a part of the tuned recipe as given in block 58.

Thus, a system incorporating the methods as described herein greatly enhances the level to which an inspection system can be optimized, because it does not require that a new scan of the substrate be performed after each parameter threshold adjustment. One reason for this is that the frame data includes not only defect information, such as location information, but also threshold information in regard to the level of the detected anomaly in relation to the parameter threshold.

Figure 7:
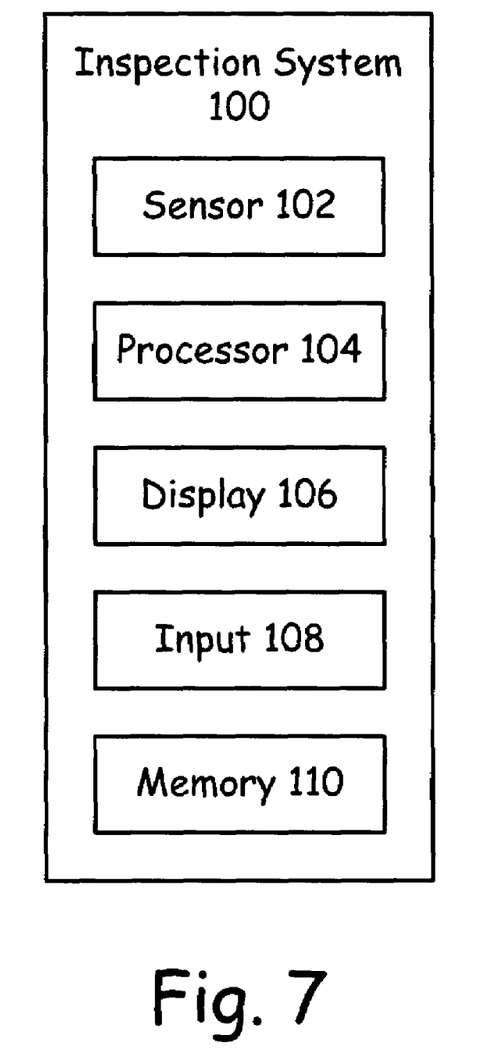
FIG. 7 is a functional block diagram of an inspection system according to a preferred embodiment of the invention.

With reference now to FIG. 7 there is depicted an inspection system 100 having sensors 102 adapted to sense characteristics of an inspection piece. A processor 104 analyzes the sensed characteristics to identify anomalies having location information and level information, analyzes the level information of the anomalies with an initial set of thresholds of inspection system parameters, and flags as defects an initial portion of the anomalies based on the immediately preceding analysis of the level information. A display 106 displays a summary of the flagged anomalies and an operating curve of potential flagged defects versus threshold for at least one of the inspection system parameters. An input 108 selectively changes the at least one of the inspection system parameters to form a modified set of thresholds of the inspection system parameters. The processor 104 further analyzes the level information of the anomalies with the modified set of thresholds of the inspection system parameters, and flags as defects an updated portion of the anomalies based on the immediately preceding analysis of the level information. The display 106 further displays an updated summary of the flagged anomalies. A memory 110 stores the modified set of thresholds of the inspection system parameters for use in an inspection system recipe.

More detail is now provided in regard to certain aspects of the invention. Various embodiments of the present invention comprehend a general software tool, an apparatus, and a method for tuning the parameters of a defect detection algorithm such as one employed to detect defects on a substrate such as a semiconductor wafer that consists of a planar surface with a plurality of dice on it. A defect detection algorithm typically examines one or more captured images of the dice, compares similar images at each pixel location and uses a discriminant function to determine differences between the images. If a difference is detected, the function further determines whether or not that difference should be flagged as a defect on the substrate.

The discriminant function preferably uses a set of parameters that controls the sensitivity of the algorithm. These parameters usually have to be individually and manually optimized for a given substrate by layer type, such as the material and types of geometry that are digitized by the scanning system and fed to the detection algorithm. The parameters are preferably optimized to maximize the number of defects of interest, or in other words defects that affect product yield, that are detected and flagged as such, while minimizing the number of nuisance events detected. A nuisance event is a defective pixel or other imaging anomaly that is flagged as a defect by the algorithm but in fact does not affect yield. Measurement noise, variations in film thickness from one die to the next, and metal grain are examples of events that might be flagged as defects but do not affect semiconductor product yield.

The generalized parameter tuner preferably displays a set of one or more operating curves showing the number and type of defects detected as a function of each algorithm parameter. Of course, this information can also be presented as bar charts, tables of numbers, pie charts, or other suitable formats. However, the central concept is that of allowing the user to select one or more operating points in the parameter space and immediately view the algorithm performance without having to rescan the substrate on the inspection system. The algorithm performance view can be, for example, in the form of defect counts by type, or a two dimensional substrate map showing where the defects lie on the substrate surface or as a stacked die map showing where the defects lie relative to each die.

An important aspect of the generalized parameter tuner is the ability to update the display of curves, charts, or maps as the user modifies the operating points in the parameter space. If a given parameter is a function of the other parameters, then changing that parameter value causes all the other operating curves to change appropriately.

The defect detection algorithm can be defined as a generalized function $F(\ )$ with n parameters, $P1, P2, \ldots Pn$, where $F(p1, p2, \ldots pn)$ denotes the number of defects detected by the algorithm for parameter values of $P1=p1$, $P2=p2, \ldots Pn=pn$. The function F can take on several forms. For example, in some cases, F can be written as the sum of r separable functions $F(p1, p2, pn)=F1(p1, p2, \ldots)+F2(p1, p2, \ldots)+ \ldots Fr(p1, p2 \ldots)$. This may be the case, for example if each die is divided into r regions and $Fi(\ )$ denotes the defects found for the given parameter setting in the i th region.

In some cases, the function F may be separable in parameter space, meaning that each parameter determines a subset of the defect population as given by $F(p1, p2 \ldots pn)= F1(p1)+F2(p2)\ldots+Fn(pn)$. In other cases, some parameters are coupled and others are not, and $F(\ )$ is the sum of s separable terms, such as in for example, F(p1, p2, . . . pn)= F1(p1, p2)+F2(p3, p4) . . . Fs(pk, pn). In this example, F1 is a function of P1 and P2 but not of P3, P4, etc. In general, if the function F can be broken down into m terms, F1( ), F2( ), . . . Fm( ), where each Fi( ) is a function of n(i) parameters, P1, P2, . . . Pn(i), the user can manually tune the n(i) parameters using a set of n(i) operating curves as depicted in FIGS. 3–5.

Each solid curve shows the variation in the defect count, Fi( ) as a function of a particular parameter keeping all the other parameter values at their current operating values. Note that each solid curve shows the current operating point for the corresponding parameter, i.e. the operating value of P1=p1, P2=p2, . . . Pn(i)=pn(i). If the user modifies the operating value of parameter P1 from p1 to, say p1' as shown in FIG. 3, then all the other operating curves for Fi( ) vs. P2, Fi( ) vs. P3, etc. are changed as shown by the dotted lines. This is because each operating curve is a function showing the variation of defect count versus that parameter value, given specific values of all the other parameters. The initial operating curves (solid curves above) were the functions Fi(P1, p2, p3, . . . pn(i)), Fi(p1, P2, p3, . . . pn(i)), Fi(p1, p2, P3, p4, . . . pn(i)), . . . Fi(p1, p2, . . . Pn(i)).

If the user changes the operating value of P1 from p1 to p1', as shown in FIG. 3, the Fi(P1, p2, . . . pn(i)) curve remains unchanged, since the values of parameters P2, P3, . . . Pn(i) are still at p2, p3, . . . pn(i) respectively. However, the other curves get recomputed as shown in dotted lines to represent the functions, Fi(p1', P2, p3, p4 . . . pn(i)), Fi(p1', p2, P3, p4, . . . pn(i)), . . . Fi(p1', p2, p3 . . . Pn(i)) because P1 has changed in value from P1=p1 to P1=p1'.

If the defects are classified in some way, either manually by the user or via an automatic defect classification algorithm, then instead of showing a single operating curve of total defect count versus a given parameter value, one can split the defect count by defect type (e.g. killer, real, don't care, nuisance, etc.) or defect class (particles, pattern, color variation grain, etc.) and show a set of operating curves, one per type/class, for each parameter value as shown in FIG. 6, which depicts Fi(P1, . . . pn(i)) showing defect counts per defect type as a function of P1.

Each time any operating point is changed by the user, the display program updates the substrate map or stacked die map to display defects that are detected. If the defects are classified by type/class, the substrate map can show the type of each defect using color or other suitable icons. By modifying each parameter in turn, the user is able to instantly see the effect on the detection results and make a tradeoff between sensitivity and nuisance rate.

The system preferably consists of three major parts. The first part is to add a special data collection function to a substrate inspection scan. Thus, in addition to detecting defects during the scan of the substrate, the system also collects run time data that determines how the threshold values are set for each pixel, and how much margin with respect to the threshold values a defect is categorized as flagged or unflagged. Because the current system processes and detects defects one image frame at a time, such data is referred to as frame data. The second part is an algorithm that simulates the detection results of a given recipe in real time using the frame data. The third part is a graphical user interface, in which the system displays a summary of the simulated results of a recipe, the operating curve of each threshold parameter—or in other words the number of detected defects as a function of the threshold value—and allows the user to manipulate the threshold values and see the modified simulation results.

To use the system, the user either has an inspection result that already includes the frame data, or the user starts with a base recipe. In the latter case, the system preferably first runs the special substrate scan to collect the frame data. Then the system preferably guides the user to classify some of the defects detected in the special substrate scan. After the classification, the system preferably automatically generates an initial recipe, and takes the user to the recipe tuning phase. In the recipe tuning phase, the system preferably brings up a graphical user interface. The graphical user interface preferably consists of 1) a window showing the current threshold values and the summary of the detection results of the recipe, and 2) two windows showing the operating curves of the selected threshold parameters.

To obtain the detection summary, the system preferably performs a defect detection simulation by applying the recipe on the frame data. The system then preferably summarizes and displays the detected defects by types. Next, the system preferably computes and displays the operating curve for each threshold parameter. To compute the operating curve, the system preferably extracts the frame data of the particular threshold parameter, and transforms the frame data to the operating curve. On the operating curve, the user can see the number of detected defects of each type as a function of threshold value, and can graphically set the parameter at a desired value. When the user changes the value of a particular parameter, the system preferably reruns the simulation and displays a summary of the new detection results. The user can instruct the system to show all the detected (flagged) defects or the undetected (unflagged) defects.

Compared to traditional methods, this invention, by means of showing the operating curves, allows the user to visualize the trade-off between flagging real defects and flagging nuisances when the threshold values are tuned. Also, this invention allows the user to get real-time feedback after tuning the threshold parameters without rescanning the substrate.

The current implementation is designed for the segmented auto threshold algorithm, and the data collected as described above is specific for the segmented auto threshold algorithm. Other possible constructions of this invention include support for different detection algorithms. When this invention is applied to a different algorithm, the system preferably collects run time data specific for the detection algorithm and develops algorithms for real time simulation using the data. The manner in which the graphical user interface presents the operating curves and the detection results can also be modified in various embodiments.

The system has the following innovative features. Collection of run time frame data and detection information during an inspection scan. Real time simulation of defect detection upon entry of a new set of threshold parameters. Computing the operating curves of defect detection with respect to each individual threshold parameter in the recipe. Displaying multiple operating curves, one for each defect type, allowing the user to visualize the trade off between flagging real defects and flagging nuisances when tuning the threshold values. A graphical user interface that allows users to visualize and manipulate the threshold boundaries with respect to the defect populations by type. The ability to show flagged defects as well as unflagged defects in various forms, such as Pareto charts, substrate maps, or tabular summaries for a given threshold parameter set.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of tuning an inspection system, the method comprising the steps of:
   a. sensing characteristics of an inspection piece using the inspection system,
   b. analyzing the sensed characteristics to identify anomalies having location information and level information,
   c. analyzing the level information of the anomalies with an initial set of thresholds of inspection system parameters,
   d. flagging as defects an initial portion of the anomalies based on the analysis of the level information in step c,
   e. displaying a summary of the flagged anomalies,
   f. selectively changing at least one of the inspection system parameters to form a modified set of thresholds of the inspection system parameters,
   g. analyzing the level information of the anomalies with the modified set of thresholds of the inspection system parameters,
   h. flagging as defects an updated portion of the anomalies based on the analysis of the level information in step g,
   i. displaying a summary of the flagged anomalies,
   j. selectively repeating steps f through i, and
   k. storing the modified set of thresholds of the inspection system parameters for use in an inspection system recipe.

2. The method of claim 1, wherein the inspection system is an optical inspection system.

3. The method of claim 1, wherein the inspection piece is a semiconducting wafer.

4. The method of claim 1, wherein the characteristics of the inspection piece are surface defects.

5. The method of claim 1, further comprising the step of selectively displaying a spatial representation of the flagged anomalies on the inspection piece.

6. The method of claim 1, further comprising the step of displaying an operating curve of potential flagged defects versus threshold for at least one of the inspection system parameters, performed between steps e and f, and additionally displaying recomputed operating curves in step i.

7. The method of claim 1, wherein the inspection system senses the characteristics of the inspection piece as image frames, and the steps of the method are repeated for each image frame of the inspection piece that is sensed by the inspection system.

8. A method of tuning a recipe for an inspection system, the method comprising the steps of:
   a. receiving level information for sensed anomalies,
   b. analyzing the level information of the anomalies with an initial set of thresholds of inspection system parameters,
   c. flagging as defects an initial portion of the anomalies based on the analysis of the level information in step b,
   d. displaying a summary of the flagged anomalies,
   e. selectively changing at least one of the inspection system parameters to form a modified set of thresholds of the inspection system parameters,
   f. analyzing the level information of the anomalies with the modified set of thresholds of the inspection system parameters,
   g. flagging as defects an updated portion of the anomalies based on the analysis of the level information in step f,
   h. displaying a summary of the flagged anomalies,
   i. selectively repeating steps e through h, and
   j. storing the modified set of thresholds of the inspection system parameters for use in an inspection system recipe.

9. The method of claim 8, wherein the anomalies represent surface defects on an inspection piece.

10. The method of claim 8, further comprising the step of selectively displaying a spatial representation of the flagged anomalies.

11. The method of claim 8, further comprising the step of displaying an operating curve of potential flagged defects versus threshold for at least one of the inspection system parameters, performed between steps d and e, and additionally displaying recomputed operating curves in step h.

12. The method of claim 8, wherein the level information is received as image frames of an inspection piece, and the steps of the method are repeated for each image frame received.

13. An inspection system comprising:
   sensors adapted to sense characteristics of an inspection piece,
   a processor adapted to:
      analyze the sensed characteristics to identify anomalies having location information and level information,
      analyze the level information of the anomalies with an initial set of thresholds of inspection system parameters, and
      flag as defects an initial portion of the anomalies based on the analysis of the level information,
   a display adapted to:
      display a summary of the flagged anomalies,
   an input adapted to selectively change at least one of the inspection system parameters to form a modified set of thresholds of the inspection system parameters,
   the processor further adapted to:
      analyze the level information of the anomalies with the modified set of thresholds of the inspection system parameters, and
      flag as defects an updated portion of the anomalies based on the immediately preceding analysis of the level information,
   the display further adapted to display an updated summary of the flagged anomalies, and
   a memory adapted to store the modified set of thresholds of the inspection system parameters for use in an inspection system recipe.

14. The inspection system of claim 13, wherein the inspection system is an optical inspection system.

15. The inspection system of claim 13, wherein the inspection piece is a semiconducting wafer.

16. The inspection system of claim 13, wherein the characteristics of the inspection piece are surface defects.

17. The inspection system of claim 13, wherein the display is further adapted to selectively display a spatial representation of the flagged anomalies on the inspection piece.

18. The inspection system of claim 13, wherein the display is further adapted to display an operating curve of potential flagged defects versus threshold for at least one of the inspection system parameters, and recomputed operating curves.

19. The inspection system of claim 13, wherein the sensors produce image frames of the inspection piece, and the inspection system processes each image frame of the inspection piece.

* * * * *